(12) United States Patent
Stalcup et al.

(10) Patent No.: US 6,336,930 B1
(45) Date of Patent: Jan. 8, 2002

(54) POLYMER FILLED BONE PLATE

(75) Inventors: Gregory C. Stalcup, Columbia City; Anthony J. Lozier, Warsaw, both of IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 09/520,262

(22) Filed: Mar. 7, 2000

(51) Int. Cl.[7] .............................................. A61B 17/80
(52) U.S. Cl. ........................... 606/69; 606/76; 606/60; 606/53; 606/72
(58) Field of Search .................... 606/1, 53, 54, 606/60, 61, 69, 70, 71, 72, 76, 151, 192; 602/5, 6, 8, 13; 623/16.11, 17.11, 17.12

(56) References Cited

U.S. PATENT DOCUMENTS

| | | |
|---|---|---|
| 4,313,434 A | 2/1982 | Segal |
| 4,403,607 A | 9/1983 | Woo et al. |
| 4,662,887 A | 5/1987 | Turner et al. ................. 623/16 |
| 4,714,478 A | 12/1987 | Fischer ........................ 623/23 |
| 4,893,618 A | 1/1990 | Herzberg |
| 5,013,315 A | 5/1991 | Barrows |
| 5,102,413 A | 4/1992 | Poddar ........................ 606/62 |
| 5,303,718 A | 4/1994 | Krajicek ..................... 128/897 |
| 5,423,850 A | 6/1995 | Berger ........................ 606/192 |
| 5,437,614 A * | 8/1995 | Grim ............................ 602/19 |
| 5,480,400 A | 1/1996 | Berger ........................ 606/60 |
| 5,514,137 A | 5/1996 | Coutts ......................... 606/62 |
| 5,658,286 A | 8/1997 | Sava |
| 5,658,310 A | 8/1997 | Berger ........................ 606/192 |
| 5,681,289 A | 10/1997 | Wilcox et al. .............. 604/175 |
| 5,827,289 A | 10/1998 | Reiley et al. ................. 606/86 |
| 5,951,160 A | 9/1999 | Ronk ........................ 366/130 |
| 5,997,582 A | 12/1999 | Weiss ........................... 623/23 |

FOREIGN PATENT DOCUMENTS

| | | |
|---|---|---|
| GB | 952842 | 3/1964 |
| WO | WO 98/0903 | 10/1989 |

* cited by examiner

Primary Examiner—David O. Reip
(74) Attorney, Agent, or Firm—Todd Dawson

(57) ABSTRACT

An orthopaedic bone plate includes a flexible bag having a plurality of through holes; and a hardened polymer within the bag. The bone plate is attached to a bone by placing the bag against the bone; affixing the bag to the bone using a plurality of fasteners which extend through the bag; injecting a polymer into the bag; and hardening the polymer in the bag.

26 Claims, 6 Drawing Sheets

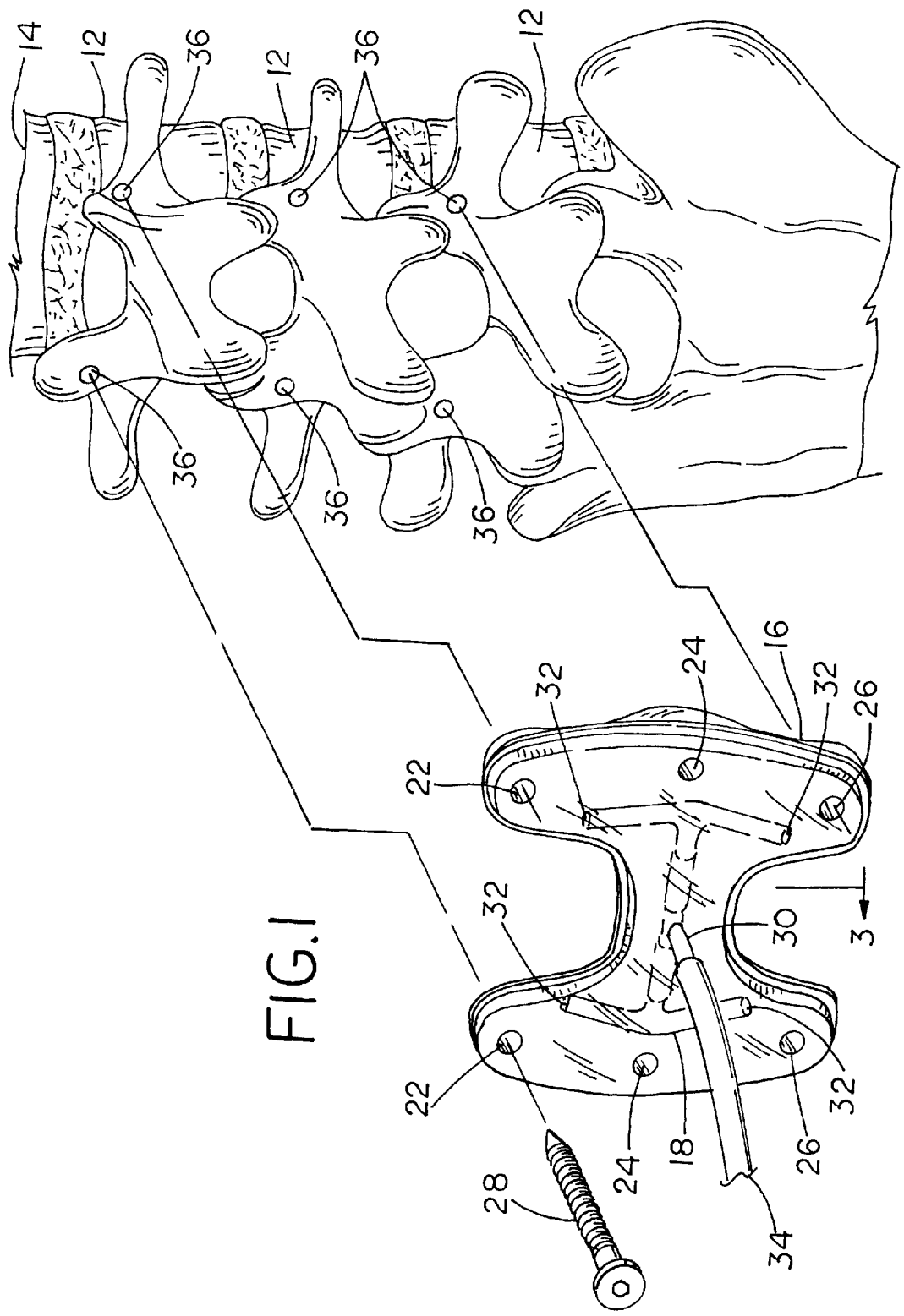

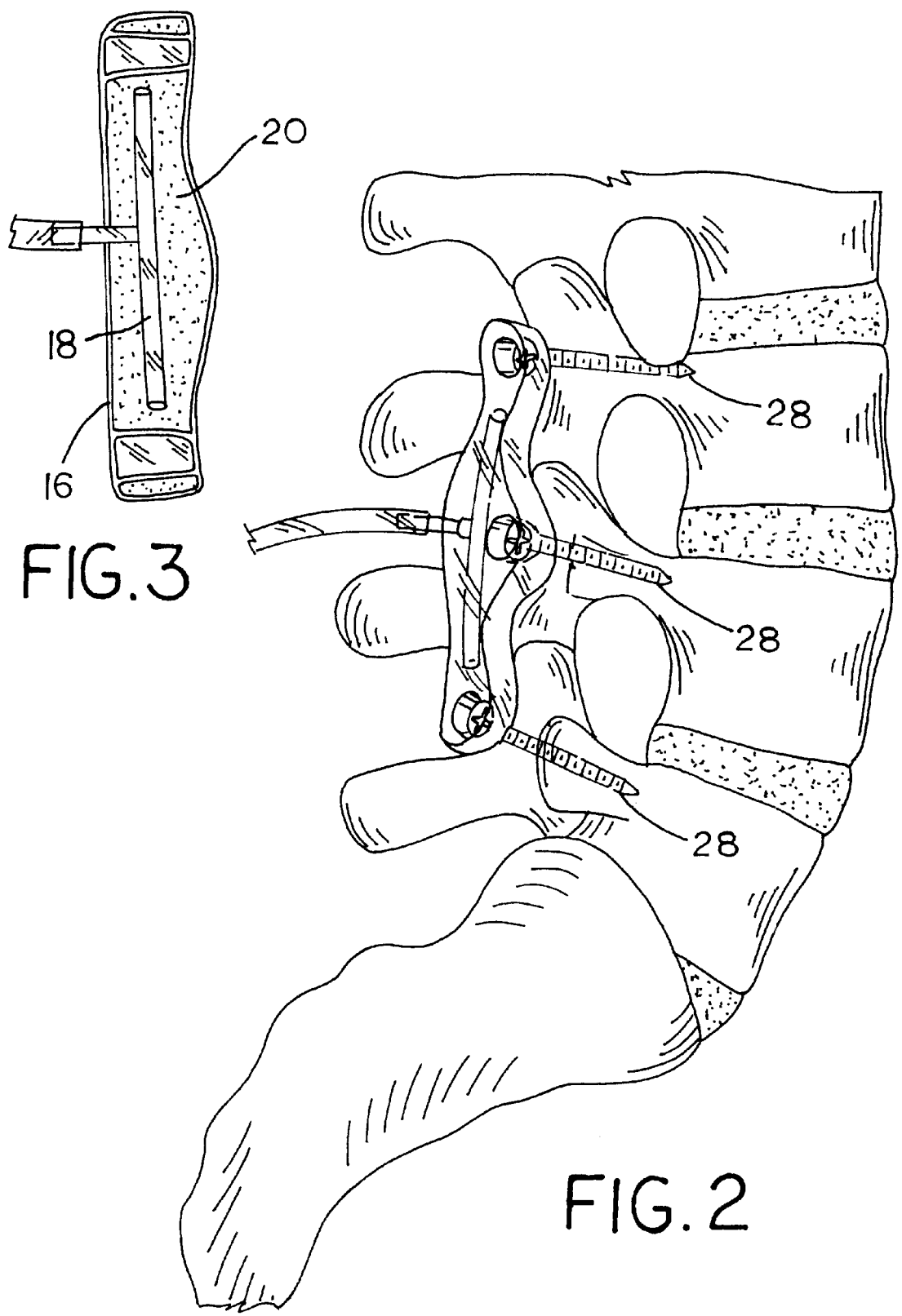

POLYMER FILLED BONE PLATE

BACKGROUND OF THE INVENTION

1. Field of the Invention

The present invention relates to orthopaedic devices, and, more particularly, to bone plates.

2. Description of the Related Art

An orthopaedic bone plate is attached to a bone and used to support different bones relative to each other, or support pieces of an individual bone during the healing process. Typically, a bone plate is manufactured to approximate the shape of a bone to which it is to be attached. The shape of the bone plate may be based upon statistical analysis of a common size and shape of a particular bone. However, since the actual size and shape of a bone may vary from one patient to another, it is often times necessary to manually deform the bone plate during surgery to achieve a proper fit. The bone plate may be placed against the bone, observed for deviation, removed from the bone and deformed using manual bending techniques. The bone plate is then placed against the bone and again visualized to determine any further necessary adjustments. This process may be somewhat time consuming during surgery.

What is needed in the art is a bone plate which is easy and fast to install, and easily contours to the shape of the bone to which it is attached.

SUMMARY OF THE INVENTION

The present invention provides an orthopaedic bone plate including a bag, structural support disposed within the bag and high strength polymer surrounding the structural support within the bag.

The invention comprises, in one form thereof, an orthopaedic bone plate including a flexible bag having a plurality of through holes; and a hardened polymer within the bag. The bone plate is attached to a bone by placing the bag against the bone; affixing the bag to the bone using a plurality of fasteners which extend through the bag; injecting a polymer into the bag; and hardening the polymer in the bag.

An advantage of the present invention is that the orthopaedic bone plate is contourable to the shape of the bone to which it is attached.

Another advantage is that a structural support may be positioned within the bag to provide enhanced structural rigidity to the bone plate.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a perspective view of an embodiment of an orthopaedic bone plate of the present invention for fixating a spine;

FIG. 2 is a side view of the orthopaedic bone plate shown in FIG. 1 attached to the spine;

FIG. 3 is a side view of the orthopaedic bone plate shown in FIGS. 1 and 2;

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 4:
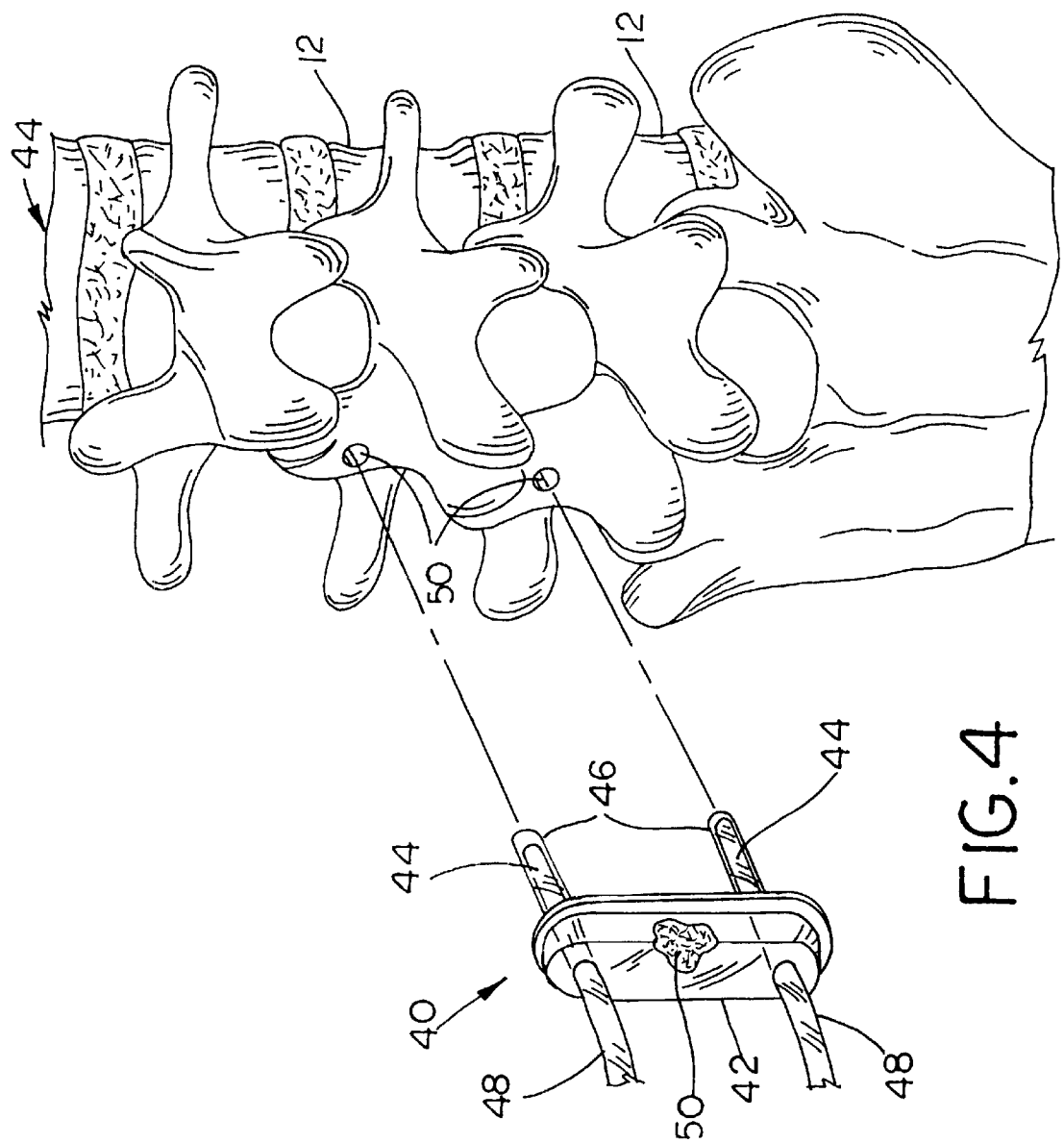
FIG. 4 is another embodiment of an orthopaedic bone plate of the present invention.

Referring now to the drawings, and more particularly to FIGS. 1–3, there is shown an embodiment of an orthopaedic bone plate 10 of the present invention which is attached and used to fixate vertebrae 12 in a spine 14.

Orthopaedic bone plate 10 generally includes a flexible bag 16, a structural support 18 disposed therein and a high strength polymer surrounding structural support 18 and disposed within bag 16. Bag 16 has a generally H-shape and is configured to fixate three sequentially adjacent vertebrae 12 relative to each other. Bag 16 has a first pair of holes 22, a second pair of holes 24 and a third pair of holes 26. Each pair of holes 22, 24 and 26 is associated with a respective vertebrae 12 and allows the passage of a fastener such as a bone screw 28 therethrough to attach orthopaedic bone plate 10 to the three associated vertebrae 12.

Bag 16 may be formed from any suitable material. Bag 16 is shown as a contoured bag with a specific H-shape in the embodiment illustrated in FIGS. 1–3. However, the material from which bag 16 is constructed may allow expansion under pressure to some extent. Moreover, bag 16 may be constructed from a porous or non-porous material allowing at least some of the polymer 20 disposed therein to flow or seep therethrough and adhere bag 16 with an adjacent bone. The porous material would provide for the venting of air as the polymer is injected into the bag.

Structural support 18 is in the form of a metal, hollow injection tube which is disposed within bag 16. Injection tube 18 includes an inlet port 30 extending from bag 16, and four outlet ports 32 which are associated with each respective leg of H-shaped bag 16. A fill hose 34 is attached with inlet port 30 at one end thereof, and with a source of pressurized polymer (not shown) at an opposing end thereof. Polymer 20 is injected under pressure through fill hose 34 and injection tube 18 to the interior of bag 16 to thus fill bag 16 at a desired fill pressure.

Polymer 20 is hardened within bag 16 to form a substantially rigid orthopaedic bone plate 10. Polymer 20 is a high strength polymer such as PMMA which is curable upon application of energy such as thermal energy, light energy or X-ray energy, or the addition of a chemical catalyst. If bag 16 is constructed as a porous bag, polymer 20 at least partially flows therethrough and may be selected to be bioresorbable.

During surgery, the posterior side of spine 14 is exposed for access to the three sequentially adjacent vertebrae 12. Orthopaedic bone plate 10 is placed over vertebrae 12 as shown in FIGS. 1 and 2. The location of pilot holes 36 on each vertebrae 12 are marked and drilled within vertebrae 12. Orthopaedic bone plate 10 may either remain in place against vertebrae 12 or be removed from vertebrae 12 during the formation of pilot holes 36. Bone screws 28 are then passed through each respective hole 22 in bag 16 and threadingly engaged within each corresponding pilot hole 36. Polymer 20 is then injected under pressure into bag 16 through fill hose 34 and injection tube 18. Polymer 20 is then hardened within bag 16 either through the application of energy such as thermal energy, light energy or X-ray energy, or the addition of a chemical catalyst prior to or during the injection process. Fill hose 34 is then detached or cut from inlet port 30. The incision is then closed over spine 14.

Referring now to FIG. 4, another embodiment of an orthopaedic bone plate 40 of the present invention is shown. Orthopaedic bone plate 40 is similar to orthopaedic bone plate 10 shown in FIGS. 1–3 in the sense that it is also used to fixate sequentially adjacent vertebrae 12 relative to each other. Orthopaedic bone plate 40 includes a flexible bag 42 and a pair of structural supports in the form of a pair of injection tubes 44 therein. Each injection tube 44 is disposed within a corresponding projection 46 extending from bag 42. A pair of fill hoses 48 are attached with each respective injection tube 44.

During surgery, the posterior side of spine 14 is exposed and orthopaedic bone plate 40 is placed adjacent to a pair of vertebrae 12 to be fixated relative to each other. Pilot holes 50 are marked and drilled in each vertebrae 12. Orthopaedic bone plate 40 is then connected with each vertebrae 12 such that each projection 46 extends into a corresponding pilot hole 50. A high strength polymer 52 is then injected under pressure into orthopaedic bone plate 40. Bag 42 is preferably constructed as a porous bag allowing polymer 52 to pass therethrough and thereby bond each projection 46 within the corresponding pilot hole 50. Polymer 52 is then hardened through the application of energy such as thermal energy, light energy or X-ray energy, or the addition of a chemical catalyst.

Figure 5:
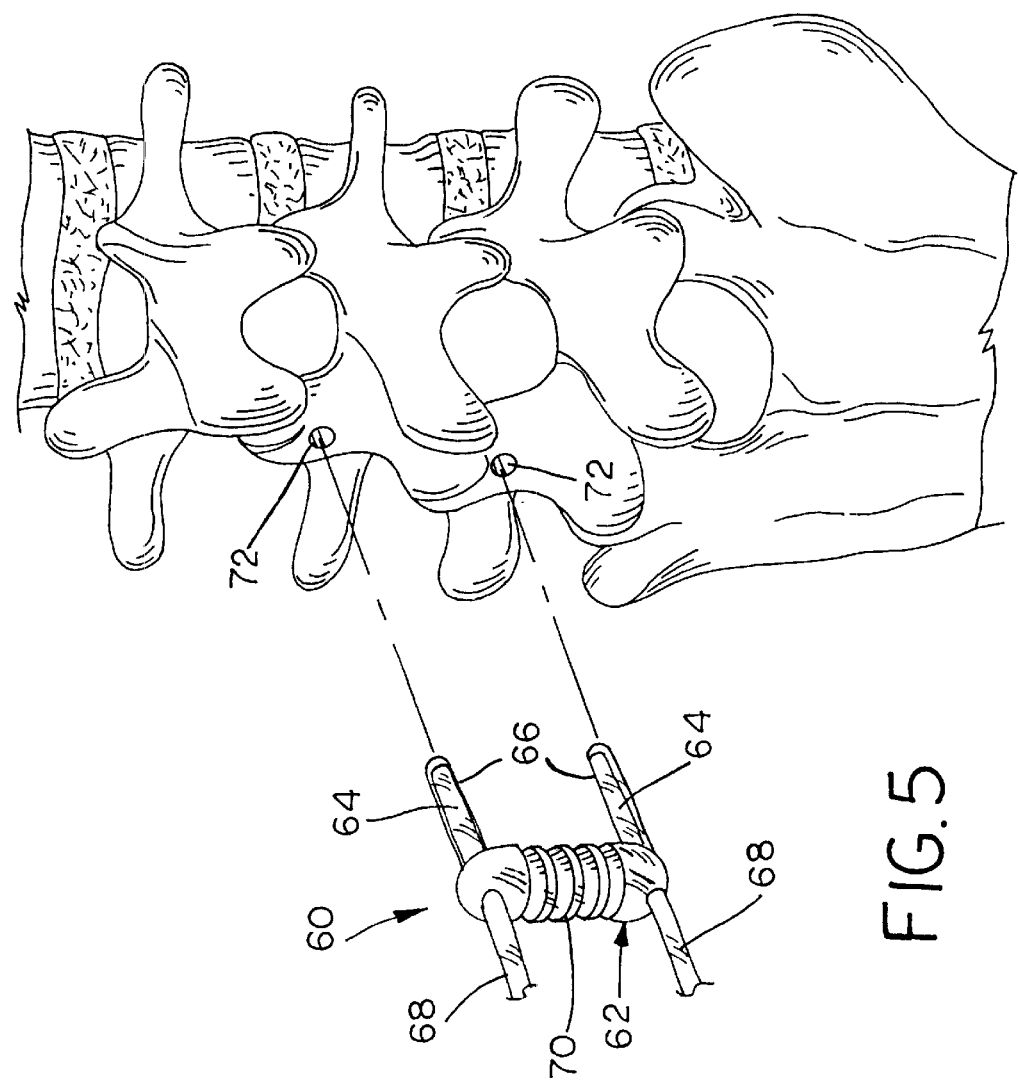
FIG. 5 illustrates yet another embodiment of an orthopaedic bone plate of the present invention.
Figure 6:
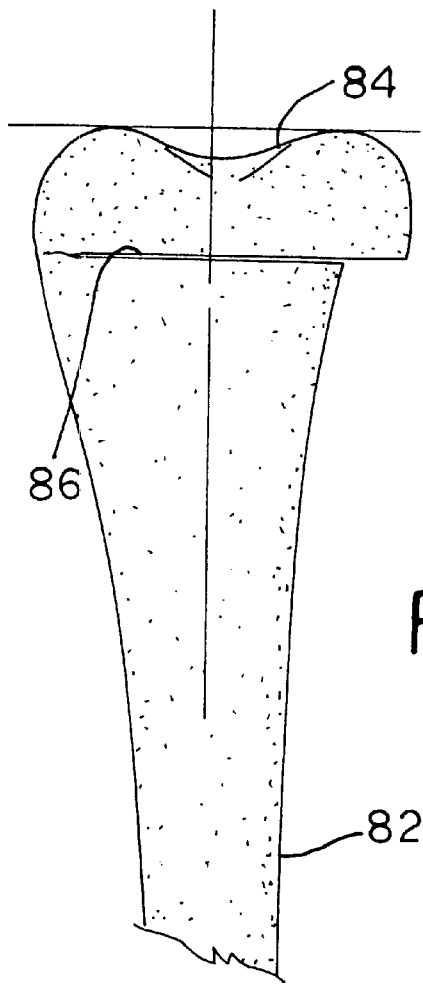
FIG. 6 is a frontal view of a cut tibia to which a bone plate of the present invention may be attached.
Figure 9:
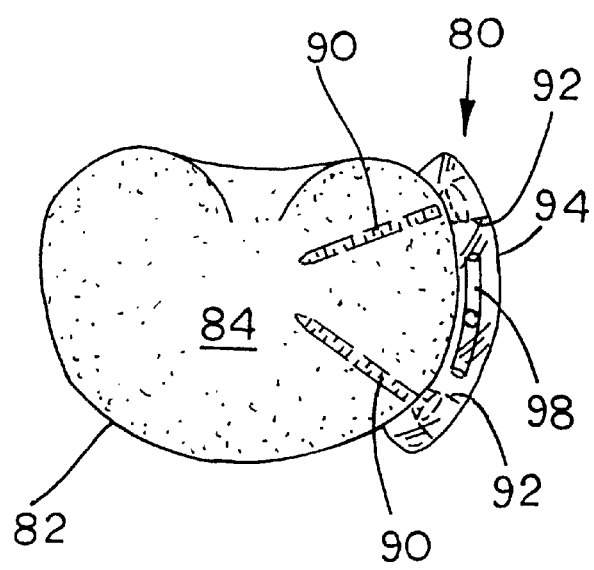
FIG. 9 is a top view of the bone plate and tibia of FIGS. 7–8, with the bone plate attached to the tibia.
Figure 8:
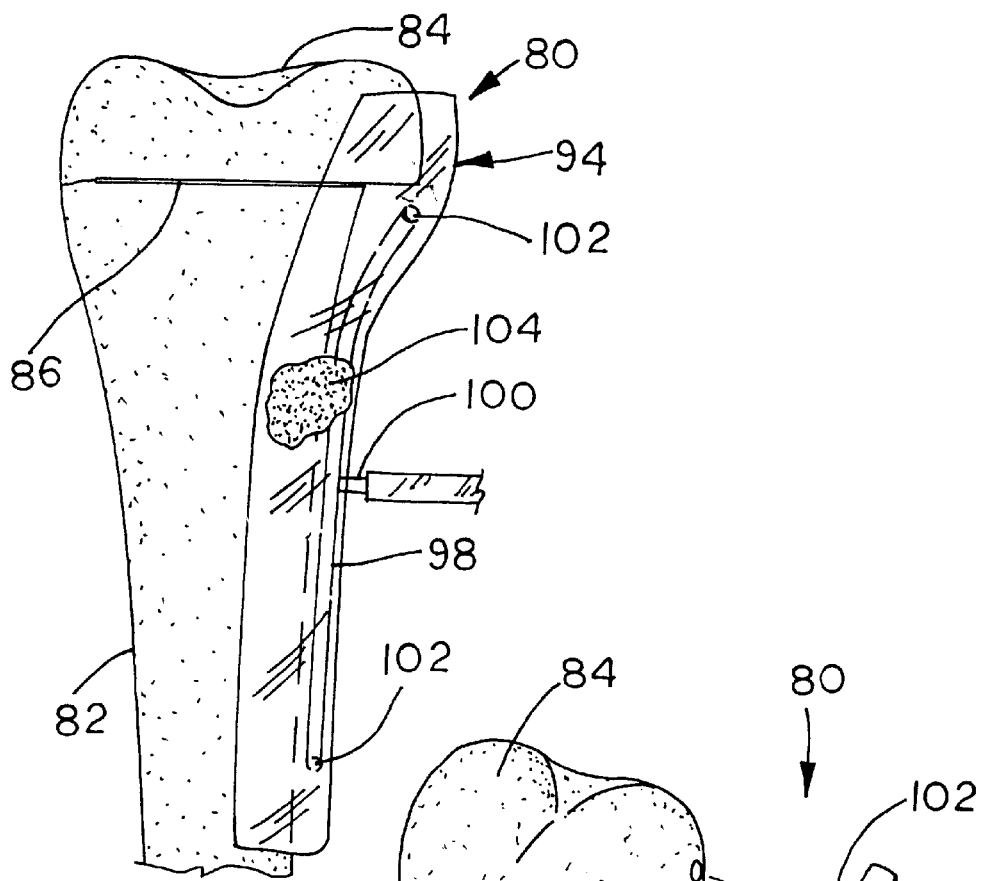
FIG. 8 is a front view of the bone plate and tibia of FIG. 7, with the bone plate placed against the tibia.
Figure 7:
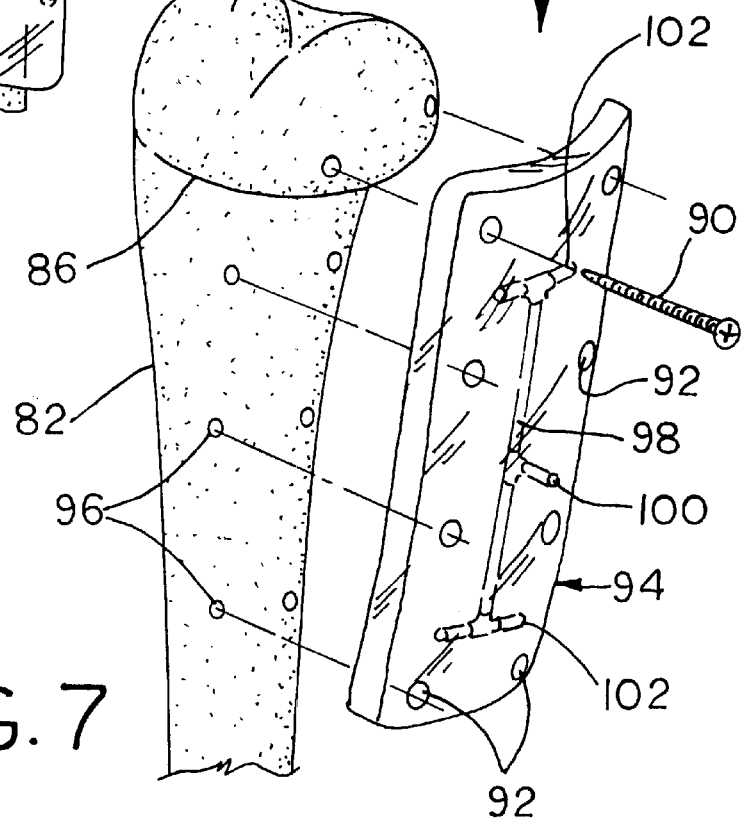
FIG. 7 is a perspective view of another embodiment of a bone plate shown in relation to the tibia of FIG. 6.

Referring to FIG. 5, another embodiment of an orthopaedic bone plate 60 of the present invention is shown. Orthopaedic bone plate 60 includes injection tube 64, projections 66 and fill hoses 68 similar to the embodiment of orthopaedic bone plate 40 shown in FIG. 5. The primary difference between orthopaedic bone plate 60 and orthopaedic bone plate 40 is that bag 62 includes an accordion shaped interconnecting portion 70 which allows the spacing and angular orientation between projection 66 to vary to some extent, depending upon the exact placement location and orientation of pilot holes 72 in vertebrae 12.

Referring now to FIGS. 6–9, there is shown another embodiment of an orthopaedic bone plate 80 of the present invention which is attached to a bone in the form of a proximal tibia 82. Tibia 82 has an articular bearing surface 84 which was not in proper alignment with a mating articular bearing surface of a distal femur. Accordingly, a wedge of bone is removed in a procedure known in the industry as a High Tibial Osteotomy. After the wedge is removed the bone surfaces are brought into contact in a known manner. Orthopaedic bone plate 80 is attached to tibia 82 using bone screws 90 which pass through through holes 92 and bag 94 and are threadingly received within pilot holes 96 in tibia 82. A structural support 98 within bag 94 includes an inlet port 100 allowing a polymer 104 to be injected under pressure through outlet ports 102 in bag 94. The polymer 104 is then hardened within bag 94.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic bone plate, comprising:
 a flexible bag having a plurality of through holes; and
 a hardened polymer within said bag.

2. The orthopaedic bone plate of claim 1, further comprising a structural support at least partially within said bag.

3. The orthopaedic bone plate of claim 2, wherein said structural support comprises a hollow injection tube for injecting said polymer.

4. The orthopaedic bone plate of claim 3, wherein said hollow injection tube is comprised of metal.

5. The orthopaedic bone plate of claim 3, wherein said hollow injection tube has a generally H-shape.

6. The orthopaedic bone plate of claim 1, wherein said bag has an H-shape.

7. The orthopaedic bone plate of claim 6, wherein said plurality of through holes comprise six through holes.

8. The orthopaedic bone plate of claim 6, wherein said bone plate is configured for use in spinal fixation.

9. The orthopaedic bone plate of claim 1, wherein said structural support is disposed entirely within said bag.

10. The orthopaedic bone plate of claim 1, wherein said polymer comprises a curable polymer.

11. The orthopaedic bone plate of claim 10, wherein said polymer is curable with one of thermal energy, light energy, X-ray energy and a chemical catalyst.

12. The orthopaedic bone plate of claim 10, wherein said polymer comprises a bioresorbable polymer.

13. The orthopaedic bone plate of claim 10, wherein said polymer comprises polymethylmethacrylate.

14. The orthopaedic bone plate of claim 1, wherein said bag comprises a porous bag allowing some of said polymer to pass therethrough.

15. A method of attaching a bone plate to a bone, comprising the steps of:
 placing a bag against the bone;
 affixing the bag to the bone using a plurality of fasteners which extend through the bag;
 injecting a polymer into said bag; and
 hardening said polymer in said bag.

16. The method of claim 15, wherein said injecting step comprises injecting said polymer under pressure into said bag.

17. The method of claim 15, wherein said affixing step occurs prior to said injecting step.

18. The method of claim 15, wherein said hardening step occurs after said injecting step.

19. The method of claim 15, further comprising a structural support at least partially within said bag.

20. The method of claim 19, wherein said structural support comprises a hollow injection tube, said injecting step being carried out using said injection tube.

21. The method of claim 20, wherein said hollow injection tube is comprised of metal.

22. The method of claim 20, comprising a fill hose attached to said injection tube, and comprising the further step of cutting off said fill hose after said injecting step.

23. The method of claim 15, wherein said bag comprises a flexible bag.

24. A method of attaching a bone plate to a bone, comprising the steps of:
- placing a bag against a bone;
- affixing the bag to the bone;
- injecting a polymer into said bag; and
- hardening said polymer in said bag.

25. An orthopaedic bone plate, comprising:
- a flexible bag, at least one structural support at least portionally within said bag, and a hardened polymer within said bag and surrounding said at least one structural support, wherein said bag includes at least one projection, each said projection having a corresponding said structural support extending at least partially therein.

26. The orthopaedic bone plate of claim 25, wherein each said projection defines a polymeric fastener for attachment with the bone.

* * * * *